(12) United States Patent
Kobayashi et al.

(10) Patent No.: US 10,317,367 B2
(45) Date of Patent: Jun. 11, 2019

(54) EDDY-CURRENT FLAW DETECTOR AND EDDY-CURRENT FLAW DETECTION METHOD

(71) Applicant: KABUSHIKI KAISHA TOSHIBA, Minato-Ku (JP)

(72) Inventors: Noriyasu Kobayashi, Yokohama (JP); Souichi Ueno, Ota (JP); Naotaka Suganuma, Yokohama (JP); Tatsuya Oodake, Zushi (JP); Takeshi Maehara, Yokohama (JP); Takashi Kasuya, Yokohama (JP); Hiroya Ichikawa, Yokohama (JP)

(73) Assignee: KABUSHIKI KAISHA TOSHIBA, Minato-Ku (JP)

( * ) Notice: Subject to any disclaimer, the term of this patent is extended or adjusted under 35 U.S.C. 154(b) by 116 days.

(21) Appl. No.: 15/525,527

(22) PCT Filed: Nov. 10, 2015

(86) PCT No.: PCT/JP2015/081620
§ 371 (c)(1),
(2) Date: May 9, 2017

(87) PCT Pub. No.: WO2016/076316
PCT Pub. Date: May 19, 2016

(65) Prior Publication Data
US 2017/0336361 A1 Nov. 23, 2017

(30) Foreign Application Priority Data
Nov. 14, 2014 (JP) .................................. 2014-231860

(51) Int. Cl.
*G01N 27/90* (2006.01)
*G21C 17/003* (2006.01)

(52) U.S. Cl.
CPC ......... *G01N 27/9046* (2013.01); *G01N 27/90* (2013.01); *G01N 27/902* (2013.01); *G01N 27/9033* (2013.01); *G21C 17/003* (2013.01)

(58) Field of Classification Search
CPC ............. G01N 27/902; G01N 27/9033; G01N 27/9053; G01N 27/82; G01N 27/90;
(Continued)

(56) References Cited

U.S. PATENT DOCUMENTS 4,849,693 A * 7/1989 Prince ................ G01N 27/9053
324/225
5,418,457 A * 5/1995 Hedengren ............ B82Y 15/00
324/225

(Continued)

FOREIGN PATENT DOCUMENTS

FR 2 689 637 A1 10/1993
JP 8-101167 A 4/1996
(Continued)

OTHER PUBLICATIONS

English machine translation of JP2006329632.*
(Continued)

*Primary Examiner* — Lee E Rodak
(74) *Attorney, Agent, or Firm* — Oblon, McClelland, Maier & Neustadt, L.L.P.

(57) ABSTRACT

An eddy-current flaw detector includes a trace data calculator configured to calculate each coordinate with respect to flaw detection points on which an inspection probe is used upon performing an eddy-current testing based on an inputted condition of eddy-current flaw detection and surface shape data of an inspection-object surface measured by a profilometer, and to calculate a normal vector of each flaw detection point; a gap evaluation calculator configured to acquire an evaluation result on a gap between the inspection-
(Continued)

object surface and the inspection probe for each flaw detection point; a flaw detection data collector configured to acquire flaw detection data of an inspection object for each flaw detection point; a flaw detection data analyzer configured to evaluate presence/absence of a flaw in the inspection-object surface based on the flaw detection data of the inspection object and the evaluation result on the gap for each flaw detection point.

10 Claims, 4 Drawing Sheets

(58) Field of Classification Search
CPC ........... G01N 27/9006; G01N 27/9046; G21C 17/003; B82Y 15/00; G01B 7/28; G01B 7/285
See application file for complete search history.

(56) References Cited

U.S. PATENT DOCUMENTS

| | | |
|---|---|---|
| 2001/0017540 A1 | 8/2001 | Arai |
| 2004/0153260 A1 | 8/2004 | Suh et al. |
| 2006/0109001 A1 | 5/2006 | Suh et al. |
| 2008/0309328 A1 | 12/2008 | Qiao et al. |
| 2013/0193960 A1* | 8/2013 | Nishimizu ......... G01N 27/9006 324/240 |
| 2014/0229149 A1* | 8/2014 | Guan ................ G01N 29/4472 703/2 |
| 2016/0123928 A1 | 5/2016 | Kobayashi et al. |

FOREIGN PATENT DOCUMENTS

| | | |
|---|---|---|
| JP | 10-325829 A | 12/1998 |
| JP | 2001-174441 A | 6/2001 |
| JP | 2006-145525 A | 6/2006 |
| JP | 2006-329632 A | 12/2006 |
| JP | 2007-147525 A | 6/2007 |
| JP | 2009-2945 A | 1/2009 |
| JP | 2012-32180 A | 2/2012 |
| JP | 2012-181097 A | 9/2012 |
| JP | 2013-242205 A | 12/2013 |
| JP | 2014-25704 A | 2/2014 |
| JP | 2014-199240 A | 10/2014 |

OTHER PUBLICATIONS

Noriyasu Kobayashi, et al., "Development of Eddy Current Testing System for Bottom-Mounted Instrumentation Nozzle in Reactor Pressure Vessel", Maintenology, vol. 13, No. 1, Total 12 Pages, (2014), (with English Translation).

Kota Nomura, et al., "Characteristics of Eddy Current Testing Using Surface Coils on Small Curvature Radius Space", Proceedings of $9^{th}$ Japan Society of Maintenology Annual Conference, Tokyo, Total 8 Pages, (2012), (with English Translation).

International Search Report dated Feb. 9, 2016 in PCT/JP2015/081620 Filed Nov. 10, 2015.

International Preliminary Report on Patentability and Written Opinion dated May 16, 2017 in PCT/JP2015/081620 (English translation only).

* cited by examiner

EDDY-CURRENT FLAW DETECTOR AND EDDY-CURRENT FLAW DETECTION METHOD

TECHNICAL FIELD

Embodiments of the present invention relate to an eddy-current flaw detector and an eddy-current flaw detection method.

BACKGROUND ART

In an aging nuclear power plant, for example, surface inspection and volumetric inspection are required in order to evaluate soundness of its in-core structures. An eddy-current testing (ECT) is known as one method of surface inspection. The ECT has an advantage that inspection can be completed in a short period, because inspection under water can be performed without draining reactor water.

However, there is a case where it may be difficult for ECT to provide good result with high inspection accuracy in dependence upon a variety of an inspection object (which includes an object to be inspected or an inspected object), in such a case that the inspection object by ECT is, for example, an in-core structure such as a bottom portion of a reactor pressure vessel (RPV). In this case, since it is difficult to move an probe (which will be hereinafter referred to as "inspection probe") for ECT exactly along the surface of the in-core structure as the inspection object, the inspection probe being configured to detect an eddy-current, a distance between the inspection probe and the inspection surface, i.e., lift-off (lift-off distance) is likely to increase or change.

Such increase or change in lift-off leads to reduction in eddy-current detection sensitivity, i.e., flaw (defect) detection sensitivity and occurrence of a false signal which indicates that a flaw is present even though the flaw is not present in (or on) the inspection object. Thus, in general, it is considered to be difficult to perform an inspection of which an inspection object has narrow and complicated parts in shape, such as a bottom portion in RPV, the inspection performed by using ECT.

Accordingly, there is a proposed technique in which actual inspection is performed after storing a contact condition between an inspection probe and an inspection surface in a memory. The stored contact condition is given by performing a teaching process which includes a step of positioning an inspection probe at each point (which will be hereinafter referred to as "flaw detection point") predetermined in order to detect flaws in/on the inspection object, and a step of setting the contact condition between the inspection probe and an inspection surface at each flaw detection point.

PRIOR ART DOCUMENT

Patent Document

[Patent Document 1] Japanese Unexamined Patent Application Publication No. 2012-181097

SUMMARY OF THE INVENTION

Problem to be Solved by the Invention

The conventional technique such as above-described technique is advantageous in that flaw detection can be performed with a short lift-off.

However, the conventional technique needs to perform the teaching procedure of selecting a contact condition for each of inspection points, and therefore has a problem that immense amount of time is required for the teaching procedure in a case where the inspection object has many inspection points (i.e., flaw detection points) for which the ECT is performed.

In view of the above-described circumstance, it is an object of the present invention to provide an eddy-current flaw detector and an eddy-current flaw detection method both of which can inspect a narrow surface of an object having a complicated shape such as a three-dimensionally changing curved-surface shape in a short time while keeping a short lift-off.

Means for Solving the Problem

In order to solve the above-described problem, an eddy-current flaw detector according to an embodiment of the present invention includes:

a trace data calculator configured to calculate each coordinate with respect to flaw detection points on which an inspection probe including a contact plane is moved and positioned to perform an eddy-current testing, the flaw detection points being predetermined on a surface of an object to be inspected based on a condition of the eddy-current flaw detection to be inputted and surface shape data of the object surface measured by a profilometer including a shape measurement sensor, and to calculate each of first normal vectors at each of the flaw detection points;

a gap evaluation calculator configured to acquire an evaluation result by evaluating a gap between the object surface and the inspection probe for each of the flaw detection points, under a condition where the inspection probe is arranged to be in contact with the object surface, a second normal vector is a normal vector of the contact plane in the inspection probe arranged on the object surface, the contact plane being calculated based on shape data of the inspection probe to be inputted and facing to the object surface upon scanning, and the second normal vector accords with the first normal vector calculated by the trace data calculator;

a flaw detection data collector configured to acquire flaw detection data of the object to be inspected for each of the flaw detection points from the inspection probe; and a flaw detection data analyzer configured to evaluate presence/absence of a flaw in the object surface based on the flaw detection data of the object to be inspected and the evaluation result, acquired for each of the flaw detection points.

In order to solve the above-described problem, an eddy-current flaw detection method according to an embodiment of the present invention is a method using an eddy-current flaw detector that includes a trace data calculator, a gap evaluation calculator, a flaw detection data collector, and a flaw detection data analyzer, and includes:

a trace data calculation step, by the trace data calculator, of calculating each coordinate with respect to flaw detection points on which an inspection probe including a contact plane is moved and positioned to perform an eddy-current testing, the flaw detection points being predetermined on a surface of an object to be inspected based on a condition of the eddy-current flaw detection to be inputted and surface shape data of the object surface measured by a profilometer, and calculating each of first normal vectors at each of the flaw detection points;

a gap evaluation step, by the gap evaluation calculator, of acquiring an evaluation result by evaluating a gap between the object surface and the inspection probe for each of the flaw detection points, under a condition where the inspection probe is arranged to be in contact with the object surface, a second normal vector is a normal vector of the contact plane in the inspection probe arranged on the object surface, the contact plane being calculated based on shape data of the inspection probe to be inputted and facing to the object surface upon scanning, and the second normal vector accords with the first normal vector calculated in the trace data calculation step;

a flaw detection data collection step, by the flaw detection data collector, of acquiring flaw detection data of the object to be inspected for each of the flaw detection points from the inspection probe; and a flaw detection data analysis step, by the flaw detection data analyzer, of evaluating presence/absence of a flaw in the object surface based on the flaw detection data of the object to be inspected acquired for each of the flaw detection points in the flaw detection data collection step and the evaluation result acquired for each of the flaw detection points in the gap evaluation step.

Effects of the Invention

According to embodiments of the present invention, eddy-current flaw detection can be performed on an inspection object having narrow and complicated surface in a short time while a lift-off is being shortly kept.

BRIEF DESCRIPTION OF THE DRAWINGS

FIG. 2 (including FIGS. 2A and 2B) illustrates a case of arrangement when an inspection probe of the eddy-current flaw detector in the one embodiment of the present invention is positioned at the closest point to a flaw detection point in an inspection object, wherein

FIG. 3 (including FIGS. 3A and 3B) illustrates evaluation of a gap (interspace) performed by a gap evaluation calculator of the eddy-current flaw detector according to the one embodiment of the present invention, wherein

DESCRIPTION OF EMBODIMENTS

Hereinafter, descriptions will be given of eddy-current flaw detectors and eddy-current flaw detection methods according to embodiments of the present invention with reference to the accompanying drawings. In the following descriptions, each term indicative of a direction such as upper, lower, right, and left is based on the state illustrated in the drawings or a normal usage state.

Figure 1:
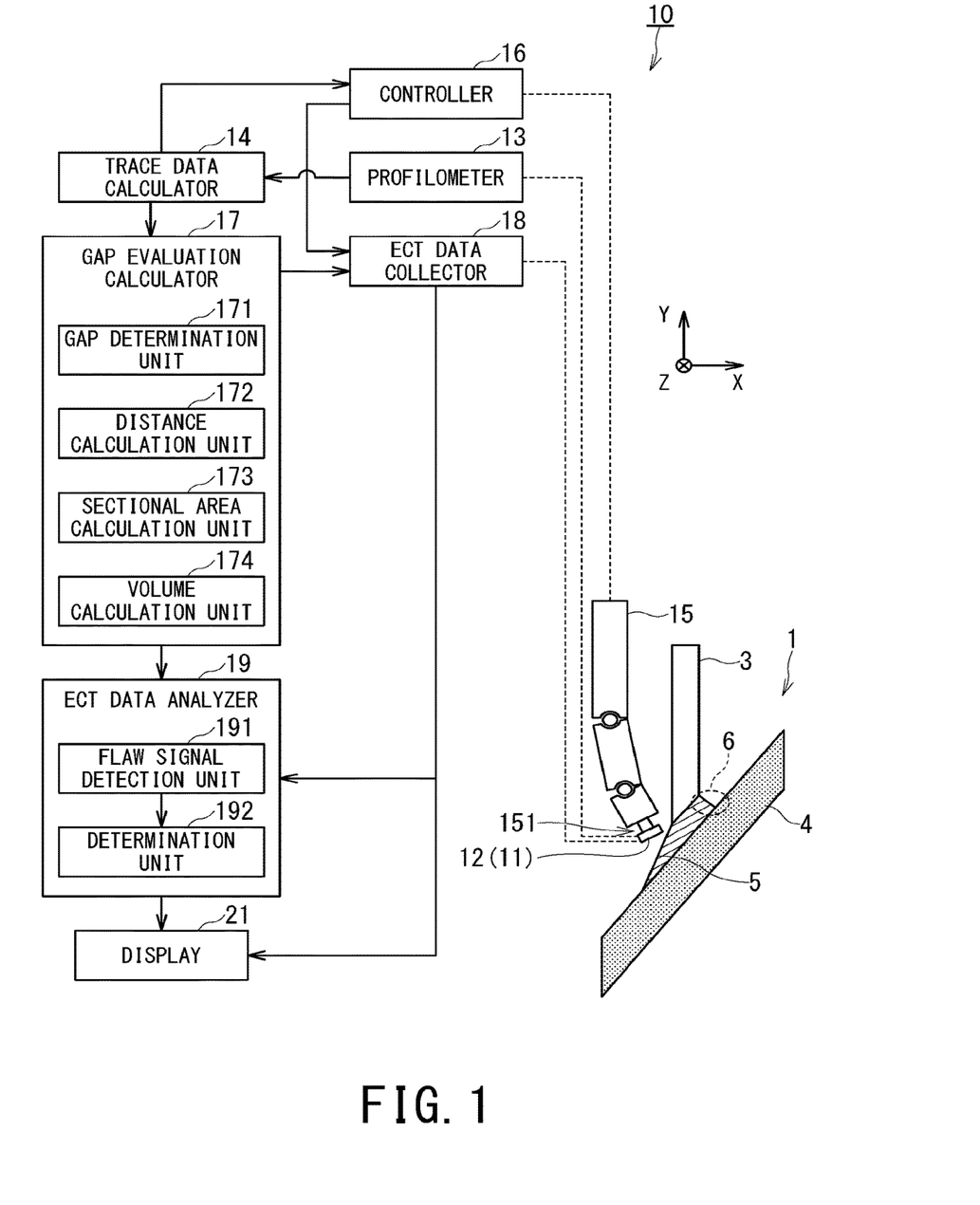
FIG. 1 is a configuration diagram illustrating configuration of an eddy-current flaw detector according to one embodiment of the present invention.

FIG. 1 is a configuration diagram illustrating configuration of an eddy-current flaw detector 10 that is one example of eddy-current flaw detectors according to embodiments of the present invention.

An inspection object 1 illustrated in FIG. 1 is an object to be inspected (or inspected object after the inspection is completed) by the eddy-current flaw detector 10, and is a structure which includes a welded portion 5. The welded portion 5 is welded area in a bottom portion 4 of a reactor pressure vessel (RPV), and is formed by welding bottom mounted instrumentation (BMI) tubes 3. The BMI tube 3 is cylindrical structure. The internal surface of the bottom portion 4 is approximately spherical, and localized shape of this entire curved surface is actually different from point to point when it is viewed three-dimensionally. In particular, the curved surface of the welded portion 5 is complicated in shape, and further includes narrow portions 6. Thus, in general, it is considered to be difficult to perform eddy-current flaw detection on the welded portion 5.

The eddy-current flaw detector 10 is an apparatus that evaluates presence/absence of a flaw in the surface (which will be hereinafter referred to as "inspection-object surface") of the inspection object 1 based on flaw detection data to be acquired as described below and evaluation result on a gap (interspace) between a bottom surface of an eddy-current flaw detection probe (which will be hereinafter referred to as "ECT probe") 12 as an inspection probe and the inspection-object surface to be evaluated (calculated) from trace data as described below. Specifically, the eddy-current flaw detector 10 generates the trace data based on conditions (which will be hereinafter referred to as "flaw detection conditions") for the inspection object 1 to be inputted and surface shape data (profile data) indicating a surface shape (profile) of the inspection object 1 which is measured on the basis of signals outputted from a shape measurement sensor 11, drives the ECT probe 12 on the basis of the generated trace data, and thereby acquires the flaw detection data of the inspection object 1 from the ECT probe 12.

The eddy-current flaw detector 10 includes, e.g., a profilometer 13, a trace data calculator 14, a driver 15, a controller 16, a gap evaluation calculator 17, an eddy-current flaw detection data collector (which will be hereinafter referred to as "ECT data collector") 18, an eddy-current flaw detection data analyzer (which will be hereinafter referred to as "ECT data analyzer") 19, and a display (screen) 21.

The profilometer 13 is configured, e.g., as a shape (profile) measurement device such as a three-dimensional measurement device, and has a function of acquiring surface shape data in accordance with output signals (sensor output) from the shape measurement sensor 11. The profilometer 13 may be configured to adopt arbitrary one or more shape measurement methods selected from general shape measurement methods such as a laser light section method and a stereo-camera method in which two cameras are used.

The profilometer 13 acquires surface shape data of the inspection object 1 on the basis of sensor output from the shape measurement sensor 11, and outputs the acquired surface shape data of the inspection object 1 to the trace data calculator 14. Namely, when the surface shape data of the inspection object 1 have been already generated, it is not necessary to newly generate the surface shape data of the inspection object 1. User may use the pre-existing surface shape data without acquiring new surface shape data.

The trace data calculator 14 has a function of calculating each coordinate (position) at each measurement point (flaw detection point) on which ECT probe 12 including the bottom surface as a contact plane is moved and positioned to perform the ECT, of calculating each normal vector (which will be hereinafter referred to as "first normal vector") at each measurement point, of calculating normal vector (which will be hereinafter referred to as "second normal vector") at the center point P0 set on the bottom surface of the ECT probe 12, and of calculating position and orientation of the ECT probe 12 with respect to each measurement point in a situation (which will be hereinafter referred to as "adjustment situation") where the ECT probe 12 can be positioned at the closest (nearest) point to the inspection object 1 without interfering (colliding against) the inspection object 1. Specifically, each coordinate and first normal vector is respectively calculated on the basis of inputted flaw detection conditions and the profile data indicating the surface shape of the inspection object 1. The second normal vector is calculated on the basis of the profile data indicating the surface shape of the ECT probe 12.

First, the trace data calculator 14 calculates each coordinate (position) and first normal vector at each measurement point (flaw detection point). There are information such as a range (flaw detection range) set on the inspection-object surface to perform the ECT, each distance between flaw detection points on the inspection-object surface from which the flaw detection data of the inspection object 1 are acquired, the origin (or reference) coordinates, i.e., reference point, the information being used as the flaw detection conditions to calculate each coordinate and first normal vector at each measurement point. Here, the coordinates mean spatial coordinates which provide with positional information in space, and is represented by an arbitrary coordinate system being capable of specifying a spatial position. The arbitrary coordinate system includes, e.g., a three-dimensional orthogonal coordinate system, in which three axes including an X axis, a Y axis, and a Z axis are perpendicular to each other, and another coordinate system which can be converted into the three-dimensional orthogonal coordinate system.

As a result of inputting the flaw detection conditions including, e.g., the flaw detection range and each distance between flaw detection points to the trace data calculator 14, the trace data calculator 14 is possible to calculate and identify each flaw detection point by shifting a position in a coordinate-axis direction from a predetermined flaw detection point within the flaw detection range at the distance between flaw detection points. Further, the trace data calculator 14 uses the respective flaw detection points and the surface shape data of the inspection object 1, and is thereby possible to calculate the respective first normal vectors at each of the flaw detection points.

Next, shape data of the ECT probe 12 are inputted to the trace data calculator 14. The trace data calculator 14 uses calculated first normal vectors and inputted shape data of the ECT probe 12, calculates a position (which will be hereinafter referred to as "closest position") at which the ECT probe 12 is arranged (positioned) as close (near) as possible to the flaw detection point without interfering with the inspection object 1 and orientation of the ECT probe 12 when the ECT probe 12 is arranged (positioned) at the closest position, and generates the trace data based on the calculated closest position and orientation. The trace data generated by the trace data calculator 14 at least include positional (coordinate) information on the respective flaw detection points, information on the respective first normal vectors corresponding to the respective flaw detection points, and the closest position (e.g., the coordinates represented by plural axes at the center point of the bottom surface of the ECT probe 12) for each flaw detection point and orientation for each flaw detection point.

After the trace data calculator 14 generates the trace data, the trace data calculator 14 transmits the trace data to the controller 16 and the gap evaluation calculator 17. The trace data calculator 14 also transmits the shape data of the ECT probe 12 and the surface shape data of the inspection object 1 to the controller 16 and the gap evaluation calculator 17. The shape data of the ECT probe 12 and the surface shape data of the inspection object 1 are used by the gap evaluation calculator 17 for calculating a sectional area or volume of the gap between the ECT probe 12 and the inspection object 1.

It is noted that the trace data may not necessarily include information on the orientation of the ECT probe 12 for each flaw detection point. Because the respective first normal vectors matches the second normal vector of the ECT probe 12 at the respective flaw detection points in the adjustment situation, the orientation (second normal vector) of the ECT probe 12 for each flaw detection point can be specified by calculating the respective first normal vectors at respective flaw detection points. This is the reason why the trace data may not necessarily include information on the orientation of the ECT probe 12 for each flaw detection point.

The driver 15 is configured as, e.g., multi-shaft type driver which is an arm including plural perpendicular drive shafts and rotational drive shafts, and includes an attachment unit 151 provided to one end (tip) of the arm. The attachment unit 151 is configured to detachably attach both the shape measurement sensor 11 and the ECT probe 12. Namely, the attachment unit 151 may be configured to hold any one of the shape measurement sensor 11 and the ECT probe 12 by replacing each other, and be configured to hold both the shape measurement sensor 11 and the ECT probe 12 without replacing each other. The driver 15 drives the drive shafts thereof, moves the attachment unit 151 to desired position and orientation, and thereby changes and keeps position and orientation of the shape measurement sensor 11 or the ECT probe 12 attached to the attachment unit 151 in desired state.

The driver 15 receives drive control data from the controller 16, controls driving of the respective shafts on the basis of the received drive control data, and thereby changes a position and orientation of the device (i.e., the shape measurement sensor 11 or the ECT probe 12) attached to the attachment unit 151. If the surface shape data of the inspection object 1 is acquired, the driver 15 changes the position and orientation of the shape measurement sensor 11. If the ECT is performed, the driver 15 changes the position and orientation of the ECT probe 12.

The controller 16 has a function of controlling the driver 15. The controller 16 generates a control signal of controlling the position and orientation of the attachment unit 151, transmits generated control signal to the driver 15, and thereby controls the position and orientation of the attachment unit 151.

The controller 16 generates drive control data to control the driver 15 (i.e., the position and orientation of the attachment unit 151) on the basis of the trace data acquired from the trace data calculator 14 and identification information indicating which of the shape measurement sensor 11 and the ECT probe 12 is attached to the attachment unit 151. The drive control data at least include operation data (each-axis operation data) for each of plural drive shafts of the driver 15. After the controller 16 generates the drive control data, the controller 16 respectively transmits the generated drive control data to the driver 15 and the ECT data collector 18.

When the driver 15 receives the drive control data from the controller 16, the driver 15 uses the received drive control data the for the purpose of controlling the position and orientation of the attachment unit 151, and thereby moves the attachment unit 151 to desired position and orientation. Accordingly, the eddy-current flaw detector 10 is possible to sequentially perform ECT in a short time while a lift-off is being shortly kept for each flaw detection point. Meanwhile, when the ECT data collector 18 receives the drive control data from the controller 16, the ECT data collector 18 associates the flaw detection data with each flaw detection point, and uses the associated flaw detection data with reference to the drive control data.

The gap evaluation calculator 17 has a function of evaluating a gap between the inspection-object surface and the bottom surface (contact surface) of the ECT probe 12 by acquiring at least one evaluation index of the gap for each flaw detection point on the basis of the trace data generated by the trace data calculator 14. Incidentally, the gap evaluation calculator 17 may use the shape data of the ECT probe 12 and the surface shape data of the inspection object 1 in addition to the trace data, as needed, when the gap evaluation calculator 17 evaluate the gap. The evaluation index of the gap (between the bottom surface of the ECT probe 12 and the inspection-object surface) includes gap information such as information on presence/absence of a gap, distance between the bottom surface of the ECT probe 12 and the inspection-object surface, i.e, length (height) of the gap, an area (which will be hereinafter referred to as "gap sectional area") of the cross-section obtained by virtually cutting the gap in a direction of the first normal vector at the flaw detection point, and volume of the gap.

The gap evaluation calculator 17 includes, e.g., a gap determination unit 171, a distance calculation unit 172, a sectional area calculation unit 173, and a volume calculation unit 174. The gap determination unit 171 has a function of determining presence/absence of a gap. The distance calculation unit 172 has a function of calculating distance of the gap (i.e., lift-off distance). The sectional area calculation unit 173 has a function of calculating a sectional area of the gap. The volume calculation unit 174 has a function of calculating volume of the gap.

The gap evaluation calculator 17 calculates, e.g., presence/absence of a gap, distance of the gap, sectional area of the gap, volume of the gap for each flaw detection point, and thereby acquires calculation result as the evaluation index. The gap evaluation calculator 17 evaluates the gap for each flaw detection point on the basis of the acquired evaluation index, and transmits the evaluation result on the gap for each flaw detection point to the ECT data analyzer 19. The evaluation result on the gap for each flaw detection point may be also transmitted to the ECT data collector 18.

As for specific manners of evaluating the gap to be performed by the respective units of the gap evaluation calculator 17 (i.e., the gap determination unit 171, the distance calculation unit 172, the sectional area calculation unit 173, and the volume calculation unit 174), they will be described below with reference to FIG. 3.

The ECT data collector 18 applies a magnetic field to the inspection object 1 from the ECT probe 12 at each of the plural flaw detection points which are predetermined, detects a reaction magnetic field at each of the flaw detection points from the inspection object 1, and thereby acquires the flaw detection data of the inspection object 1 for each flaw detection point. Specifically, the ECT data collector 18 associates the flaw detection data with each flaw detection point by using the transmitted drive control data, and thereby acquires and collects the flaw detection data of the inspection object 1 for each flaw detection point.

There is a case where the ECT data collector 18 receives the evaluation results of the gap at each flaw detection point from the gap evaluation calculator 17. In this case, the ECT data collector 18 may generate information in which each flaw detection point is associated with the evaluation results of the gap at each flaw detection point as the flaw detection data of the inspection object 1. Further, in this case, the eddy-current flaw detector 10 may be configured to allow the display 21 to display the evaluation results of the gap at each flaw detection point and a waveform of each detection signal included in the flaw detection data of the inspection object 1, before the ECT data analyzer 19 analyzes the flaw detection data in detail.

The ECT data analyzer 19 determines reliability of the detected flaw signal, i.e., degree (i.e., certainty) of probability that the detected flaw signal is true (correct), on the basis of the flaw detection data of the inspection object 1 acquired by the ECT data collector 18 and the evaluation results transmitted from the gap evaluation calculator 17. The ECT data analyzer 19 further determines whether a flaw exists in the inspection object 1 or not in consideration of the determined degree (certainty).

The ECT data analyzer 19 includes, e.g., a flaw signal detection unit 191 and a determination unit 192. The flaw signal detection unit 191 detects a flaw signal indicative of existence of a flaw from the flaw detection data of the inspection object 1 acquired by the ECT data collector 18. The determination unit 192 determines reliability of the flaw signal detected by the flaw signal detection unit 191.

The flaw signal detection unit 191 has a function of detecting flaw signals (including a false flaw signal) indicating that a flaw exists in the inspection object 1 from the flaw detection data of the inspection object 1.

Here, flaw signals detected by the flaw signal detection unit 191 include both of a true (i.e., correct) flaw signal and a false flaw signal. The true flaw signal is attributed to a flaw actually existing in the inspection object 1. Meanwhile, the false flaw signal is a flaw signal caused by false detection, the flaw signal being faultily detected as a signal indicating that a flaw exists in the inspection object 1 tough the flaw does not exist in the inspection-object surface, i.e., a noise. Accordingly, there may be a case where the flaw signal detection unit 191 erroneously detects a false flaw signal in addition to a case where the flaw signal detection unit 191 correctly detects the correct flaw signal.

The determination unit 192 has a function of determining degree of probability that the flaw signal detected by the flaw signal detection unit 191 is a true flaw signal (i.e., reliability of the flaw signal) on the basis of the evaluation results inputted from the gap evaluation calculator 17.

The determination unit 192 first determines how the lift-off distance is long (large) on the basis of the evaluation result on the gap. In a case where the determination unit 192 first determines that the lift-off distance is zero (i.e., the ECT probe 12 is in contact with the inspection-object surface), the detected flaw signal is surely the correct flaw signal because the false flaw signal is never generated in this case. Thus, in this case, the determination unit 192 adds information, which indicates reliability of the flaw signal detected at the flaw detection point with a very high probability, to the evaluation on presence/absence of a flaw on the inspection-object surface, thereby generates information on more specific evaluation by adding the evaluation on presence/absence of the flaw to the information indicating reliability of the flaw signal, and then outputs generated information to the display 21.

Meanwhile, the false flaw signal is generated in a case where the lift-off distance (sectional area or volume) is a positive value. Thus, the detected signal as the flaw signal is probably the false flaw signal in this case. Accordingly, the determination unit 192 adds information, which indicates a high probability that the flaw signal detected at the flaw detection point is a false flaw signal, to the evaluation on presence/absence of a flaw in the inspection-object surface, and thereby generates information on more specific evaluation by adding the evaluation on presence/absence of the flaw to the information indicating high probability that the flaw signal is the false flaw signal, and then outputs generated information to the display 21.

Further, the determination unit 192 may determine reliability of each flaw signal on the basis of criteria other than the evaluation result on the gap transmitted from the gap evaluation calculator 17, the criteria being used for determining degree (i.e., certainty) of probability that the detected flaw signal is correct or not. When the determination unit 192, e.g., acquires a true flaw signal and/or a false flaw signal from a test piece made of the same substance as that of inspection object 1 in advance, the determination unit 192 may use the acquired flaw signal (true flaw signal and/or a false flaw signal) as the criteria for determining degree of probability that the detected flaw signal is correct or not. In a case where false flaw signals are previously acquired under various conditions that a gap is generated, the determination unit 192 selects the false flaw signal as a reference from the previously acquired false flaw signals under the same conditions, compares a phase of the detected flaw signal with a phase of the false flaw signal acquired under the same conditions (or conditions being as close to the conditions on the ECT as possible when there is no false flaw signal acquired under the same conditions), as a reference, and can therefore enhance accuracy in determining whether the flaw signal detected by the flaw signal detection unit 191 is merely a false flaw signal or a true flaw signal, i.e., a flaw signal on which a flaw signal attributed to a flaw actually existing on the inspection-object surface is imposed.

As described above, when the determination unit 192 determines reliability of a flaw signal on the basis of the true flaw signal and/or the false flaw signal which are previously acquired from a test piece of the same material and are used as a reference, the determination unit 192 may determine the reliability of the detected flaw signal in consideration of determination based on the evaluation on presence/absence of a flaw in the inspection-object surface in addition to determination based on the flaw signal as the reference. Instead of acquiring a true flaw signal and/or a false flaw signal from a test piece of the same material in advance, another method may be used as a reference for determining reliability of a detected flaw signal. For example, a computer performing a three-dimensional magnetic-field analysis may perform the three-dimensional magnetic-field analysis on a case where a magnetic field is applied to the same inspection object 1, acquire calculational flaw detection data from generated on a result analyzed by the three-dimensional magnetic-field analysis, and use the calculational flaw detection data as the reference for determining reliability of a detected flaw signal.

Next, a description will be given of a case of determination methods as to reliability of a flaw signal (i.e., certainty that a flaw signal is correct) to be performed by the determination unit 192 under the assumptions that the determination unit 192 determine reliability of the flaw signal by plural stages such as five-grade (e.g., level 1 to level 5) evaluation, and acquires false flaw signals which can be used as the reference and the evaluation index (such as distance, a sectional area, or volume) of the gap from which the reference selected form the false flaw signals is acquired.

Incidentally, as to assumed plural stages, it is assumed that lower level number indicates lower reliability. That is, the lowest reliability of a flaw signal corresponds to level 1 and the highest reliability of a flaw signal corresponds to level 5.

The determination unit 192 refers to the evaluation result on the gap for the flaw detection point of the flaw detection data from which a flaw signal is detected. As a result of referring the evaluation result, if the lift-off distance is zero, the determination unit 192 determines that the certainty for the flaw signal detected at the flaw detection point is level 4 (i.e., there is a high probability that this flaw signal is correct). In contrast, if the lift-off distance (sectional area or volume) is a positive value, the certainty for the flaw signal detected at the flaw detection point is level 2 (i.e., there is a low probability that this flaw signal is correct).

Further, the determination unit 192 selects a false flaw signal acquired under the same conditions as the evaluation results on the gap (or conditions as close as possible when there is not a false flaw signal acquired under the same conditions), as a reference signal, and compares the detected flaw signal with this reference signal in terms of phase and amplitude. As a result of the comparison, if the determination unit 192 acquires correlation between the detected flaw signal and the reference signal is high, the determination unit 192 decreases the level number by 1. In contrast, if the acquired correlation between the detected flaw signal and the reference signal is low, the determination unit 192 increases the level number by 1.

As the result, when a gap is generated at a flaw detection point where a flaw signal is detected and this flaw signal is determined to have high correlation with the reference signal acquired under the same conditions, this flaw signal is classified into level 1. When a gap is not present at a flaw detection point where a flaw signal is detected (i.e., distance, a sectional area, or volume is zero) and this flaw signal is determined to have low correlation with the reference signal acquired under the same conditions (i.e., a signal acquired from a test piece which does not include any flaw), this flaw signal is classified into level 5.

Note that the above described method of determining reliability of a flaw signal is merely one case selected from various methods of determining reliability of a flaw signal. That is, a determination method being capable of applying method of determining reliability of a flaw signal is not limited to the above described determination method. For example, as the simplest determination method, reliability of a flaw signal may be determined by two grades evaluation consisting of the first case where a gap exists (i.e., a case where it is determined that a gap exists or a case where distance, a sectional area, or volume is a positive value) and the second case where a gap does not exist (i.e., a case where it is determined that a gap does not present (exist) or a case where distance, a sectional area, or volume is zero).

The ECT data analyzer 19 generates the evaluation results about presence/absence of a flaw in the inspection-object surface in the above manner, and transmits the generated evaluation results to the display 21. The display 21 displays the transmitted evaluation results thereon. Here, the transmitted evaluation results to the display 21 may include information on the classification, i.e., level number, in accordance with the reliability of a flaw signal detected at the flaw detection point where the flaw signal detection unit 191 determines that a flaw is present in the inspection object 1. For example, the eddy-current flaw detector 10 enables the display 21 to display the flaw detection point, where a flaw may exist, together with the degree of reliability of the flaw signal by using a method of distinguishably displaying the degree of reliability of the flaw signal such as the plural colors corresponding to the plural levels.

The display 21 is configured by a device having a display function, such as display, monitor, and screen. The display 21 is configured to display information such as the flaw detection data of the inspection object 1 acquired by the ECT data collector 18 and evaluation results transmitted from the ECT data analyzer 19 as to presence/absence of a flaw in the inspection-object surface.

Although the above-described eddy-current flaw detector 10 includes the profilometer 13, the trace data calculator 14, the driver 15, the controller 16, the gap evaluation calculator 17, the ECT data collector 18, the ECT data analyzer 19, and the display 21, the eddy-current flaw detector 10 does not necessarily need to include the profilometer 13, the driver 15, the controller 16, and the display 21. The eddy-current flaw detector 10 may be configured by omitting one, two, three, or all of those components 13, 15, 16, and 21 from the components included in the above-described eddy-current flaw detector 10.

Although the above-described eddy-current flaw detector 10 includes the gap evaluation calculator 17 providing with the gap determination unit 171, the distance calculation unit 172, the sectional area calculation unit 173, and the volume calculation unit 174, the gap evaluation calculator 17 does not necessarily need to include all of the gap determination unit 171, the distance calculation unit 172, the sectional area calculation unit 173, and the volume calculation unit 174. That is, the gap evaluation calculator 17 may include at least one unit selected from the gap determination unit 171, the distance calculation unit 172, the sectional area calculation unit 173, and the volume calculation unit 174, in the eddy-current flaw detector 10. In short, it is sufficient for eddy-current flaw detector 10 that the gap evaluation calculator 17 has only to acquire at least one evaluation index.

Next, a description will be specifically given of calculating a position where the ECT probe 12 can be positioned as close as possible to the flaw detection point without interfering with (colliding against) the inspection object 1, as to the trace data generation by the trace data calculator 14.

Figure 2A:
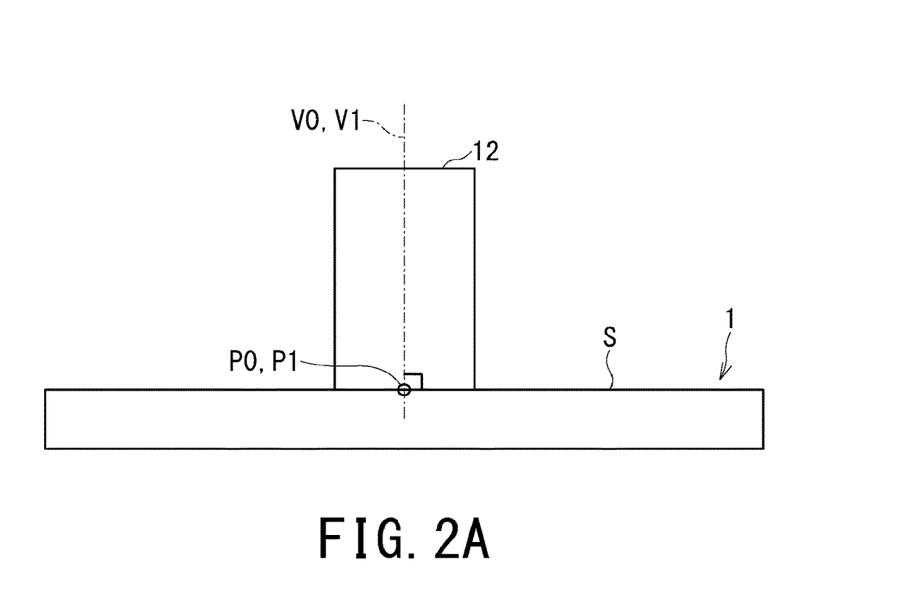
FIG. 2A is a schematic diagram when the surface of the inspection object is flat and FIG. 2B is a schematic diagram when the surface of the inspection object is curved.
Figure 2B:
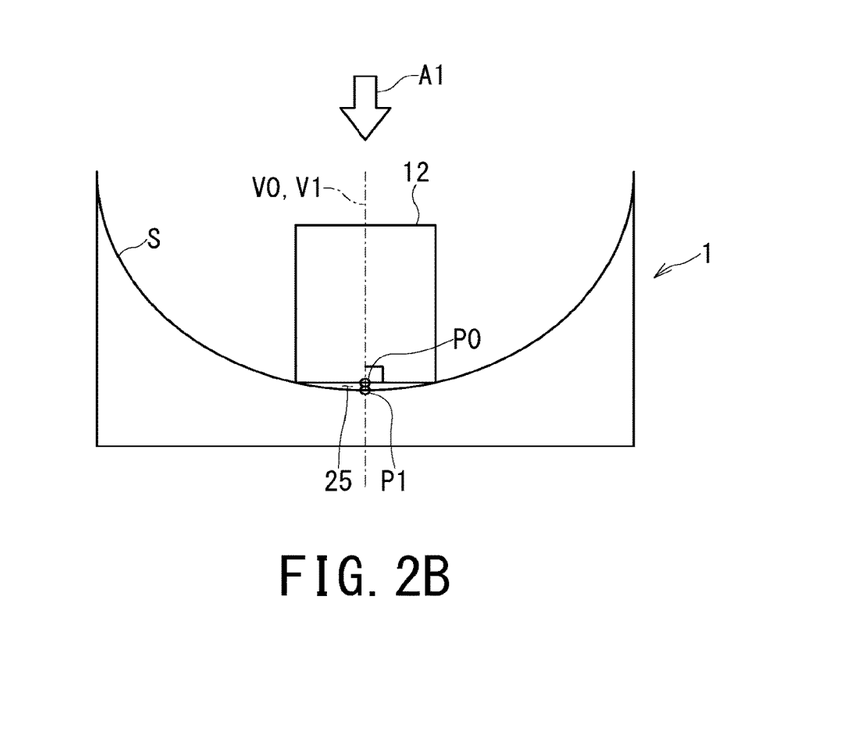

FIG. 2 including FIG. 2A and FIG. 2B illustrates the case of arrangement when the ECT probe 12 is positioned at the closest point to a flaw detection point P1 in the inspection object 1. Here, FIG. 2A is a schematic diagram when the inspection-object surface is flat, and FIG. 2B is a schematic diagram when the inspection-object surface is curved.

The trace data calculator 14 aligns the first normal vector V1 at the flaw detection point P1 of the inspection object 1 with the normal vector V0 which is perpendicular to the bottom surface of the ECT probe 12 (i.e., the flat plane or contact plane of the ECT probe 12 oriented toward the side of the inspection object 1 at the time of scanning) and passes through the center point P0 of this flat plane (contact plane). The trace data calculator 14 virtually moves the center point P0 close to the flaw detection point P1 (from the upper side to the lower side) until the ECT probe 12 contacts with (reaches) the inspection-object surface, while keeping the state where the normal vector V0 matches the normal vector V1.

There is a case where the surface S of the inspection object 1 (i.e., inspection-object surface) is flat at the flaw detection point P1, as illustrated in FIG. 2A. In this case, the center point P0 can be matched with the flaw detection point P1 because the entire bottom surface (contact surface) of the ECT probe 12 contacts with the inspection object 1 (i.e., inspection-object surface S). That is, the flaw detection point P1 is a position where the ECT probe 12 is the closest to the inspection object 1 without interfering with (colliding against) the inspection object 1, and the distance between the center point P0 and the flaw detection point P1 which are coincident with each other is therefore zero.

There is a case where the inspection-object surface S is curved at the flaw detection point P1, as illustrated in FIG. 2B. In this case, the ECT probe 12 can be moved (transferred) up to the point where the outer edge of the bottom surface of the ECT probe 12 contacts with the inspection object 1 (inspection-object surface S), by moving the ECT probe 12 closer to the inspection object 1, i.e., in the direction of the arrow A1 illustrated in FIG. 2B. However, if it is tried to move the center point P0 further close to the flaw detection point P1 by moving the ECT probe 12, the ECT probe 12 collides against the inspection object 1.

Thus, when the inspection-object surface S is curved at the flaw detection point P1, the closest position of the ECT probe 12 is the position where the outer edge of the bottom surface of the ECT probe 12 contacts with the inspection object 1 (inspection-object surface S). In this case, the center point P0 where the ECT probe 12 is positioned at the closest position to the inspection object 1 is not coincident with the flaw detection point P1, and is therefore separated from the flaw detection point P1. That is, the gap 25 is generated between the inspection-object surface S and the bottom surface of the ECT probe 12 in this case.

Next, a description will be given of the evaluation on the gap 25 to be performed by the gap evaluation calculator 17 included in the eddy-current flaw detector 10.

Figure 3A:
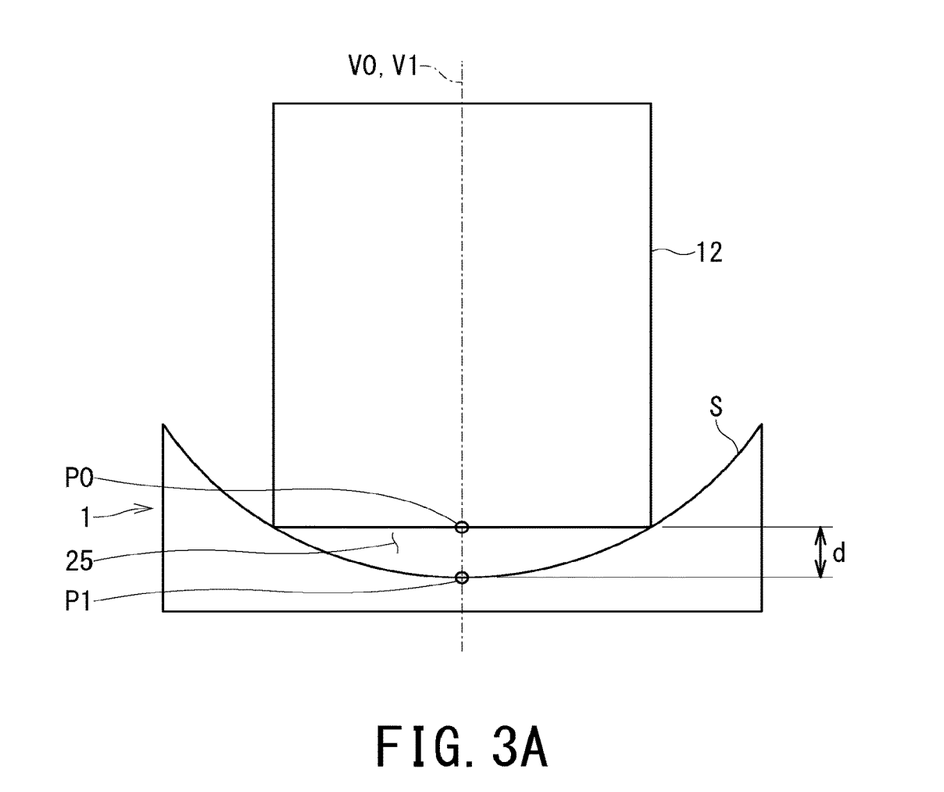
FIG. 3A is a schematic diagram illustrating distance d of the gap and FIG. 3B is a schematic diagram illustrating a gap sectional area $S_G$ of the gap and volume $V_G$ of the gap.
Figure 3B:
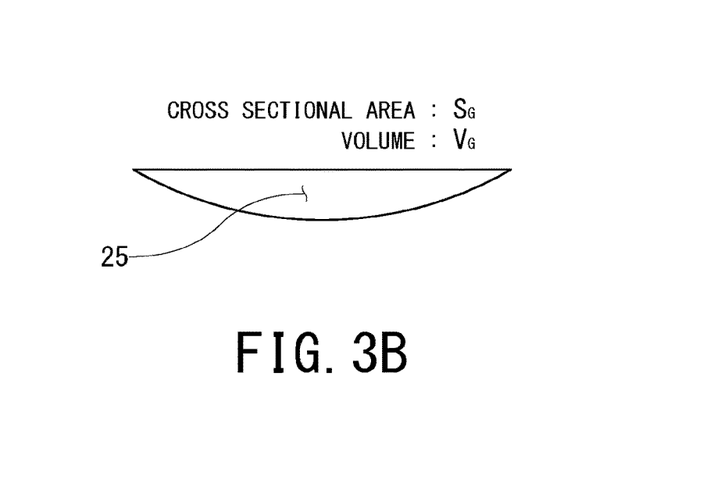

FIG. 3 including FIGS. 3A and 3B illustrates the evaluation of the gap 25 performed by the gap evaluation calculator 17. Here, FIG. 3A is a schematic diagram illustrating distance d between the two points (i.e., the flaw detection point P1 and the center point P0 of the bottom surface of the ECT probe 12) to be calculated by the distance calculation unit 172. Further, FIG. 3B is a schematic diagram illustrating a gap sectional area $S_G$ of the gap 25 to be calculated by the sectional area calculation unit 173 and a volume $V_G$ of the gap 25 to be calculated by the volume calculation unit 174.

There is the gap evaluation calculator 17 which is illustrated in FIG. 1 and includes the gap evaluation calculator 17 includes the gap determination unit 171, the distance calculation unit 172, the sectional area calculation unit 173, and the volume calculation unit 174. In the illustrated gap evaluation calculator 17, the four units 171 to 174 provide calculation results as the evaluation results on the gap 25 as follows: the gap determination unit 171 provides a determination result as to presence/absence of the gap 25; the distance calculation unit 172 provides a calculation result of the distance d of the gap 25; the sectional area calculation unit 173 provides a calculation result of the sectional area $S_G$ of the gap 25; and the volume calculation unit 174 provides a calculation result of volume $V_G$ of the gap 25.

The gap determination unit 171 determines, e.g., whether the flaw detection point P1 matches the center point P0 of the bottom surface (i.e., contact surface) of the ECT probe 12 or not. Additionally or alternatively, the gap determination unit 171 calculates the distance d between the inspection-object surface S and the bottom surface of the ECT probe 12 to be arranged (positioned) at the closest position as illustrated in FIG. 3A. The gap determination unit 171 determines presence/absence of the gap 25 between the ECT probe 12 and the inspection object 1 in accordance with whether the distance d is zero or not. The determination result on presence/absence of the gap 25 is one of the evaluation results on the gap 25.

The distance calculation unit 172 calculates the distance d from the bottom surface of the ECT probe 12 to the inspection-object surface S illustrated in FIG. 3A on the basis of, e.g., the coordinates of the flaw detection point P1 positioned on the surface of the inspection object 1 and the coordinates of the center point P0 of the bottom surface of the ECT probe 12 to be arranged (positioned) at the closest position. The distance d is one of the evaluation results on the gap 25.

The sectional area calculation unit 173 calculates a gap sectional area $S_G$, i.e., an area of the (vertical) cross-section obtained by virtually cutting the gap 25 along a flat plane which is perpendicular to the bottom surface (i.e., contact surface) of the ECT probe 12 or perpendicular to the inspection-object surface at the flaw detection point (i.e., in the direction of the normal vector V0 or V1), by using the trace data, the shape data of the ECT probe 12, and the surface shape data of the inspection object 1. The calculation result of the gap sectional area $S_G$ is one of the evaluation results on the gap 25.

Incidentally, there are various cases where the gap 25 is virtually cut at different position or in different direction. In these cases, the calculation result of the gap sectional area $S_G$ may be different value in accordance with a condition where the gap 25 is virtually cut. Thus, the sectional area calculation unit 173 receives position information of the reference point set on the bottom surface of the ECT probe 12, and azimuth angle information indicating an azimuth angle between a reference straight line which passes through the reference point and has an azimuth angle of zero degree and another straight line which passes through the reference point and has an azimuth angle, and thereby specifies the position and azimuth (direction) of the flat plane by which the gap 25 is virtually cut. Here, the reference point, the reference straight line (i.e., a direction of which the azimuth angle is zero degree) and the azimuth angle are designated by user.

For example, the eddy-current flaw detector 10 may be configured to allow the sectional area calculation unit 173 to select a maximum value as the sectional area $S_G$ from the sectional area values calculated by changing the above-described azimuth and position on the bottom surface of the ECT probe 12. As another example, the eddy-current flaw detector 10 may be configured to allow the sectional area calculation unit 173 to calculate the sectional area $S_G$ under a predetermined condition where the gap 25 is virtually cutting by a flat plane which passes through a predetermined position (e.g., the center point on the bottom surface of the ECT probe 12) and is a predetermined direction (e.g., a direction of which an azimuth angle is zero degree), and to thereby acquire the calculated sectional area $S_G$.

The volume calculation unit 174 calculates the volume $V_G$ of the gap 25 by using the trace data, the shape data of the ECT probe 12, and the surface shape data of the inspection object 1. There may be a case where the gap 25 includes non-illustrated depth (i.e., dimension in the direction perpendicular to the sheet of FIG. 2 or 3) and is not enclosed in the non-illustrated depth direction. Thus, for example, the gap 25 is treated as an enclosed space which is enclosed by the three planes (a) to (c) as follows: (a) the inspection-object surface S; (b) a flat plane including the bottom surface of the ECT probe 12; and (c) a plane which is extension of the entire side surface (lateral face) of the ECT probe 12 extending from its bottom surface to the inspection-object surface S (surface of the inspection object 1). The volume calculation unit 174 calculates volume of the enclosed space emerged by above-described treatment, and considers the calculation result (volume value) as the volume $V_G$ of the gap 25. The calculation result considered as the volume $V_G$ of the gap 25 is one of the evaluation results on the gap 25.

Next, a description will be given of the eddy-current flaw detection method according to one embodiment of the present invention.

The eddy-current flaw detection method according to one embodiment of the present invention is a method of (a) generating trace data from conditions of eddy-current flaw detection for the inspection object 1 to be inputted and the surface shape data of the inspection object 1 to be measured on the basis of signals outputted from the shape measurement sensor 11 and then (b) evaluating presence/absence of a flaw in the inspection-object surface on the basis of the flaw detection data acquired by driving the ECT probe 12 in accordance with the generated trace data and the evaluation results of the gap 25 (FIG. 2B). The eddy-current flaw detection method according to the one embodiment of the present invention can be performed by, e.g., using the eddy-current flaw detector 10.

Figure 4:
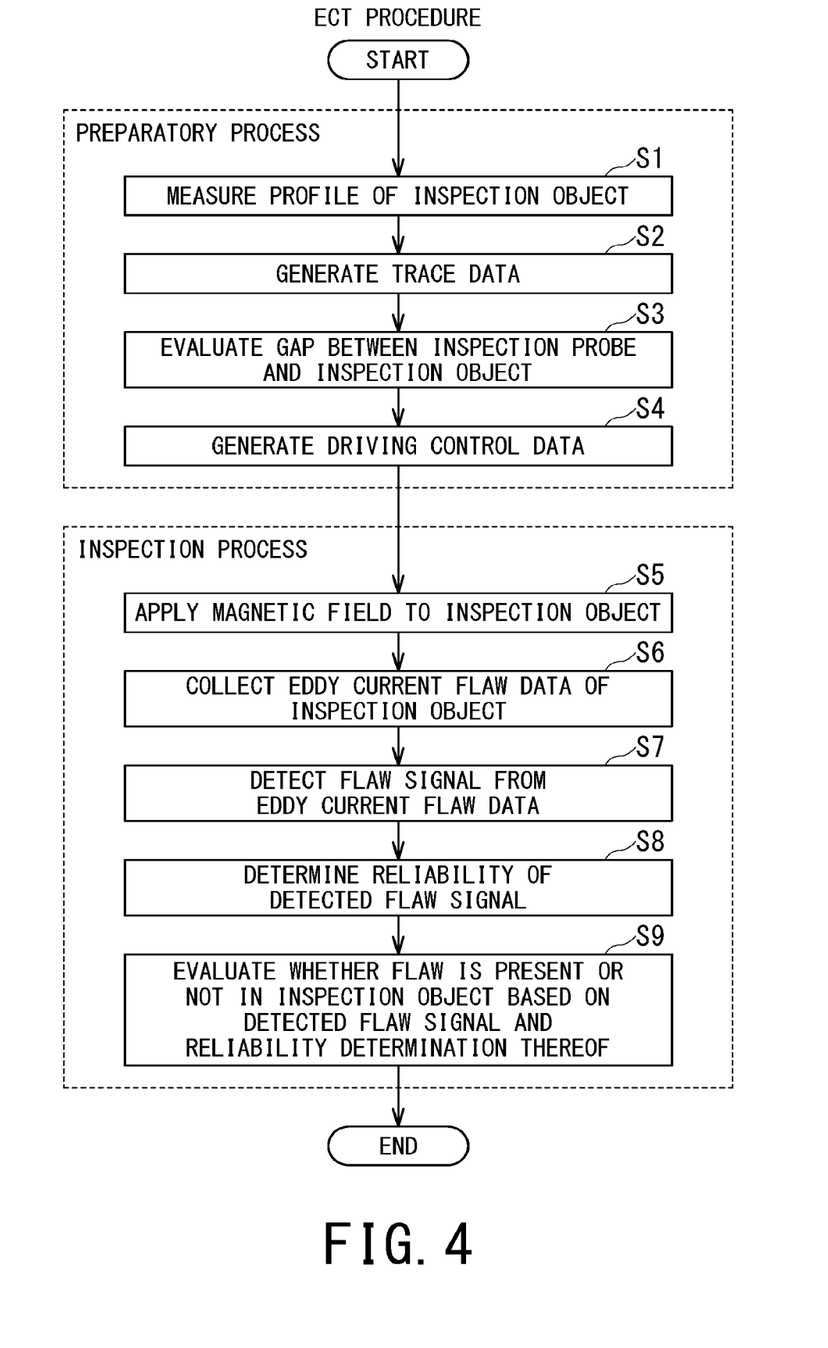
FIG. 4 is a flowchart illustrating an eddy-current flaw detection procedure performed by the eddy-current flaw detector according to the one embodiment of the present invention.

FIG. 4 is a flowchart illustrating processing (which will be hereinafter referred to as "ECT procedure") of the eddy-current flaw detection (i.e., steps S1 to S9) performed by the eddy-current flaw detector 10 (FIG. 1) according to the one embodiment of the present invention.

The ECT procedure includes steps S1 to S9, and is roughly divided into the preparatory process of the eddy-current flaw detection (ECT) including the steps S1 to S4 and the inspection process including the steps S5 to S9 for performing the ECT on the inspection object 1 illustrated in FIG. 1.

The ECT procedure includes, e.g., a profile measurement step S1, a trace data generation step S2, a gap evaluation step S3, a driving-control-data generation step S4, a magnetic-field application step S5, a flaw detection-data collection step S6, a flaw signal detection step S7, a flaw signal reliability determination step S8, and a flaw evaluation step S9.

The ECT procedure is started when the eddy-current flaw detector 10 receives an execution request. In FIG. 4, a time when the ECT procedure is started corresponds to the expression "START" illustrated in FIG. 4. After the ECT procedure is started, first, the preparatory process including the steps S1 to S4 is performed. In the preparatory process including the steps S1 to S4, first, the profile measurement step S1 is performed.

In step S1, the profilometer 13 acquires the surface shape data (profile data) of the inspection object 1 on the basis of output signals from the shape measurement sensor 11. In completion of acquiring the surface shape data of the inspection object 1, step S1 is completed, and then the trace data generation step S2 is performed.

In step S2, the trace data calculator 14 generates the trace data from the inputted flaw detection conditions and the surface shape data of the inspection object 1. In completion of generating the trace data, step S2 is completed, and then the gap evaluation step S3 is performed.

In step S3, the gap evaluation calculator 17 evaluates a gap between the inspection-object surface S and the bottom surface (i.e., contact surface) of the ECT probe 12 by an evaluation index related to the gap. In completion of evaluating on the gap, step S3 is completed, and then the driving-control-data generation step S4 is performed.

In step S4, the controller 16 generates driving control data on the basis of the trace data and identification information on a device (i.e., the shape measurement sensor 11 or the ECT probe 12) attached to the attachment unit 151. In completion of generating driving control data, step S4 is completed. Following explanation will be described as a case where the identification information indicates that the ECT probe 12 is attached to the attachment unit 151 because the inspection process will be performed in subsequent steps S5 to S9.

In completion of step S4, the preparatory process is completed, and then the inspection process including the steps S5 to S9 is started. That is, the eddy-current flaw detection (ECT) for the inspection object 1 is started as the inspection process. In the inspection process including the steps S5 to S9, first, the magnetic-field application step S5 is performed.

In step S5, the ECT data collector 18 applies a magnetic field to the inspection object 1 from the ECT probe 12. In completion of applying the magnetic field to the inspection object 1, step S5 is completed, and then the flaw-detection-data acquisition step S6 is performed.

In step S6, the ECT data collector 18 acquires flaw detection data of the inspection object 1 for each of plural flaw detection point to be set. In completion of acquiring the flaw detection data of the inspection object 1 at each law detection point, step S6 is completed, and then the flaw signal detection step S7 is performed.

In step S7, the flaw signal detection unit 191 included in the ECT data analyzer 19 determines presence/absence of a flaw signal indicating that existence of a flaw in the inspection object 1 from all the flaw detection data acquired in step S6. Here, if the flaw signal detection unit 191 determines that the flaw signal is present in the acquired flaw detection data, the flaw signal detection unit 191 detects the flaw signal. In completion of determining whether the flaw signal is present or not (absent) and detecting the flaw signal when the flaw signal detection unit 191 determines the flaw signal is present, step S7 is completed, and then the flaw signal reliability determination step S8 is performed.

In step S8, the determination unit 192 included in the ECT data analyzer 19 determines reliability of the flaw signal detected in step S7 on the basis of the evaluation result on the gap acquired in step S3. In completion of determining reliability of the flaw signal, step S8 is completed, and then the flaw evaluation step S9 is performed.

In step S9, the determination unit 192 of the ECT data analyzer 19 evaluates presence/absence of a flaw in the surface of the inspection object 1 illustrated in FIG. 1 on the basis of the flaw signal detected in step S7 and the determination result of reliability of the flaw signal determined in step S8. In completion of the evaluation on presence/absence of a flaw, the step S9 is completed.

If the flaw evaluation step S9 is completed, the entire processing of the ECT procedure including steps S1 to S9 is completed. That is, in completion of step S9, a flow of the ECT procedure illustrated in FIG. 4 proceeds to "END".

Although the above-described ECT procedure is performed in a case where step S3 is performed prior to step S4, it is not necessarily required that step S3 and the step S4 are sequentially performed. Both steps S3 and S4 may be performed in parallel after completion of step S2.

According to the eddy-current flaw detector 10 and the eddy-current flaw detection method to inspect the inspection object 1 with the use of the eddy-current flaw detector 10 as described above, the eddy-current flaw detector 10 generates each-axis operation data of the driver 15 on the basis of the trace data calculated from profile data indicating a surface shape (profile) of the inspection object 1 even if the inspection object 1 includes narrow and complicated inspection-object surface S. Thus, the eddy-current flaw detector 10 allows the ECT probe 12 to approach up to the closest position to the inspection-object surface S without performing the teaching process in which contact conditions between the probe and the inspection-object surface is selected for each flaw detection point. Hence, according to the eddy-current flaw detection method using the eddy-current flaw detector 10, flaw detection can be performed on the inspection object 1 in a period shorter than conventional technology while the lift-off is being shortly kept.

Additionally, even if the inspection object 1 includes narrow and complicated inspection-object surface S, the eddy-current flaw detector 10 is configured to precisely determine whether the detected flaw signal is true or false on the basis of the evaluation result on the gap 25 between the ECT probe 12 and the inspection-object surface S, and is therefore possible to precisely determine presence/absence of a flaw in the inspection object 1 which includes a narrow inspection-object surface S with a complicated shape.

While certain embodiments have been described, these embodiments have been presented by way of instance only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An eddy-current flaw detector comprising:
   a profilometer configured to acquire surface shape data of an object to be inspected;
   a trace data calculator configured to calculate each coordinate with respect to flaw detection points on which an inspection probe including a contact plane is moved and positioned to perform an eddy-current testing, the flaw detection points being predetermined on a surface of the object based on a condition of the eddy-current flaw detection to be inputted and the surface shape data acquired by the profilometer, and to calculate each of first normal vectors at each of the flaw detection points;
   a gap evaluation calculator storing the surface shape data and shape data of the inspection probe and configured to acquire, using the surface shape data and the shape data of the inspection probe, an evaluation result by evaluating a gap between the object surface and the inspection probe for each of the flaw detection points, under conditions where (i) the inspection probe is arranged to be in contact with the object surface, and (ii) a second normal vector of the contact plane oriented toward a side of the object surface at the time of scanning matches the first normal vector calculated by the trace data calculator, the second normal vector being perpendicular to the contact plane and passes through a center point of the contact plane;
   a flaw detection data collector configured to acquire flaw detection data of the object to be inspected for each of the flaw detection points from the inspection probe; and
   a flaw detection data analyzer configured to evaluate presence/absence of a flaw in the object surface based on the flaw detection data of the object to be inspected and the evaluation result, acquired for each of the flaw detection points.

2. The eddy-current flaw detector according to claim 1, wherein the gap evaluation calculator includes a gap presence/absence determination unit configured to determines whether the gap is absent or not for each of the flaw detection points and to acquire a determination result whether the gap is absent or not for each of the flaw detection points.

3. The eddy-current flaw detector according to claim 1, wherein the gap evaluation calculator includes a distance calculation unit configured to calculate a distance between a first intersection point and a second intersection point for each of the flaw detection points and to acquire the calculated distance as the evaluation result, and wherein the first intersection point is a point where the contact plane of the inspection probe intersects with the first and second normal vectors that accord with each other, and the second intersection point is a point where the object surface intersects with the first and second normal vectors.

4. The eddy-current flaw detector according to claim 1, wherein the gap evaluation calculator includes a sectional area calculation unit configured to calculate a sectional area of a cross-section of the gap for each of the flaw detection points, the cross-section being obtained by virtually cutting the gap by a desired flat plane which includes a straight line in parallel with the first and second normal vectors being matched each other, and to acquire the calculated sectional area as the evaluation result.

5. The eddy-current flaw detector according to claim 1, wherein the gap evaluation calculator includes a volume calculation unit configured to calculate a volume of the gap for each of the flaw detection points and to acquire the calculated volume as the evaluation result.

6. The eddy-current flaw detector according to claim 1, wherein the flaw detection data analyzer includes a flaw signal detection unit configured to detect a flaw signal indicating a flaw in the object surface from the flaw detection data, and a determination unit configured to determine degree of probability that the flaw signal indicates a true flaw in the object surface, based on the detected flaw signal and the evaluation result on the gap for each of the flaw detection points acquired by the gap evaluation calculator, and is configured to evaluate whether the flaw in the object surface is present or absent based on the flaw signal and the determined degree of probability.

7. The eddy-current flaw detector according to claim 1, further comprising:
a driver including an attachment unit configured to detachably attach the flaw detection probe and the shape measurement sensor, the driver being configured to change a position and orientation of the attachment unit in a desired state; and
a controller configured to control the position and orientation of the attachment unit based on the first normal vector calculated by the trace data calculator, the shape data of the inspection probe, the shape data of the shape measurement sensor, and information to determine whether the flaw detection probe is attached to the attachment unit or the shape measurement sensor is attached to the attachment unit.

8. An eddy-current flaw detection method using an eddy-current flaw detector that includes a trace data calculator, a gap evaluation calculator, a flaw detection data collector, and a flaw detection data analyzer, the eddy-current flaw detection method comprising:
a trace data calculation step, by the trace data calculator, of calculating each coordinate with respect to flaw detection points on which an inspection probe including a contact plane is moved and positioned to perform an eddy-current testing, the flaw detection points being predetermined on a surface of an object to be inspected based on a condition of the eddy-current flaw detection to be inputted and surface shape data of the object surface measured by a profilometer, and calculating each of first normal vectors at each of the flaw detection points;
a data transmission step, by the trace data calculator, of transmitting the surface shape data of the object and shape data of the inspection probe to the gap evaluation calculator;
a gap evaluation step, by the gap evaluation calculator, of acquiring an evaluation result, using the surface shape data and the shape data of the inspection probe transmitted in the data transmission step, by evaluating a gap between the object surface and the inspection probe for each of the flaw detection points, under conditions where (i) the inspection probe is arranged to be in contact with the object surface, and (ii) a second normal vector of the contact plane oriented toward a side of the object surface at the time of scanning matches the first normal vector calculated in the trace data calculation step, the second normal vector being perpendicular to the contact plane and passes through a center point of the contact plane;
a flaw detection data collection step, by the flaw detection data collector, of acquiring flaw detection data of the object to be inspected for each of the flaw detection points from the inspection probe; and
a flaw detection data analysis step, by the flaw detection data analyzer, of evaluating presence/absence of a flaw in the object surface based on the flaw detection data of the object to be inspected acquired for each of the flaw detection points in the flaw detection data collection step and the evaluation result acquired for each of the flaw detection points in the gap evaluation step.

9. The eddy-current flaw detection method according to claim 8,
wherein the gap evaluation step includes at least one of
a gap presence/absence determination step of determining whether the gap is absence or not for each of the flaw detection points,
a distance calculation step of calculating a distance between a first intersection point and a second intersection point for each of the flaw detection points, and wherein the first intersection point is a point where the contact plane of the inspection probe intersects with the first and second normal vectors that accord with each other, and the second intersection point is a point where the object surface intersects with the first and second normal vectors,
a sectional area calculation step of calculating a sectional area of a cross-section of the gap for each of the flaw detection points, the cross-section being obtained by virtually cutting the gap by a desired flat plane which includes a straight line in parallel with the first and second normal vectors being matched each other, a volume calculation step of calculating a volume of the gap for each of the flaw detection points, and a step of acquiring the evaluation result including an determination whether the gap is absence or not for each of the flaw detection points when the gap evaluation step includes the gap presence/absence determination step, a calculation result of the distance between the first intersection point and the second intersection point for each of the flaw detection points when the gap evaluation step includes the distance calculation step, a calculation result of the sectional area of the cross-section of the gap for each of the flaw detection points when the gap evaluation step includes the sectional area calculation step, and a calculation result of the volume of the gap for each of the flaw detection points when the gap evaluation step includes the volume calculation step.

10. The eddy-current flaw detection method according to claim 8, wherein the flaw detection data analysis step includes a flaw signal detection step of detecting a flaw signal indicating a flaw in the object surface from the flaw detection data, a determination step of determining degree of probability that the flaw signal indicates a true flaw in the object surface, based on the flaw signal detected in the flaw signal detection step and the evaluation result on the gap for each of the flaw detection points evaluated in the gap evaluation step, and a step of evaluating whether the flaw in the object surface is present or absent based on the detected flaw signal and the determined degree of probability.

* * * * *